US 12,083,283 B2

(12) United States Patent
Anderson

(10) Patent No.: US 12,083,283 B2
(45) Date of Patent: *Sep. 10, 2024

(54) OXYGEN TREATMENT DEVICE FOR MAMMALS

(71) Applicant: ERGO-FLEX TECHNOLOGIES, LLC, Conroe, TX (US)

(72) Inventor: J. T. Anderson, Conroe, TX (US)

(73) Assignee: Ergo-Flex Technologies, LLC, Conroe, TX (US)

(*) Notice: Subject to any disclaimer, the term of this patent is extended or adjusted under 35 U.S.C. 154(b) by 632 days.

This patent is subject to a terminal disclaimer.

(21) Appl. No.: 17/151,515

(22) Filed: Jan. 18, 2021

(65) Prior Publication Data

US 2021/0138177 A1 May 13, 2021

Related U.S. Application Data

(63) Continuation of application No. 15/914,888, filed on Mar. 7, 2018, now Pat. No. 10,894,139.

(Continued)

(51) Int. Cl.
*A61M 16/10* (2006.01)
*A61B 5/00* (2006.01)
(Continued)

(52) U.S. Cl.
CPC ......... *A61M 16/101* (2014.02); *A61B 5/0022* (2013.01); *A61M 16/12* (2013.01);
(Continued)

(58) Field of Classification Search
CPC ..... A61B 5/04; A61B 5/04085; A61B 5/0476; A61B 5/0492; A61B 5/08; A61B 5/0816; A61B 5/082; A61B 5/085; A61B 5/087; A61B 5/0878; A61B 5/145; A61B 5/1455; A61B 5/14551; A61B 5/14553; A61B 5/282; A61B 5/296; A61B 5/369; A61B 5/4818; A61B 5/4836; A61B 5/6803; A61H 33/14; A61J 17/001; A61J 7/0053; A61K 33/00; A61M 16/00; A61M 16/0003;
(Continued)

(56) References Cited

U.S. PATENT DOCUMENTS 4,681,099 A * 7/1987 Sato ................... A61M 16/0677
128/207.18
4,686,974 A * 8/1987 Sato .................... A61M 16/024
128/207.18

(Continued)

OTHER PUBLICATIONS

USPTO Non-Final Office Action for U.S. Appl. No. 15/914,888 dated Dec. 9, 2019.

(Continued)

*Primary Examiner* — Annette Dixon
(74) *Attorney, Agent, or Firm* — Tumey L.L.P.

(57) ABSTRACT

Method and apparatus varies the oxygen concentration level of air delivered to a person for treatment on training purposes. The apparatus includes a display device for displaying current physiological data as well as data from previous sessions for comparison purpose. The oxygen level is precisely controlled by a central processing unit in response to input data from the person.

7 Claims, 1 Drawing Sheet

Related U.S. Application Data

(60) Provisional application No. 62/619,387, filed on Jan. 19, 2018.

(51) Int. Cl.
  *A61M 16/12* (2006.01)
  *A63B 23/18* (2006.01)
  *A61B 5/021* (2006.01)
  *A61B 5/024* (2006.01)
  *A61B 5/08* (2006.01)
  *A61B 5/11* (2006.01)
  *A61B 5/145* (2006.01)
  *A61M 16/00* (2006.01)
  *A61M 16/06* (2006.01)

(52) U.S. Cl.
  CPC ............. *A63B 23/18* (2013.01); *A61B 5/021* (2013.01); *A61B 5/024* (2013.01); *A61B 5/0816* (2013.01); *A61B 5/1118* (2013.01); *A61B 5/14542* (2013.01); *A61B 5/4836* (2013.01); *A61B 5/4839* (2013.01); *A61B 5/4866* (2013.01); *A61B 2503/10* (2013.01); *A61B 2505/09* (2013.01); *A61M 2016/003* (2013.01); *A61M 16/024* (2017.08); *A61M 16/06* (2013.01); *A61M 2016/103* (2013.01); *A61M 2202/0208* (2013.01); *A61M 2205/52* (2013.01); *A61M 2230/06* (2013.01); *A61M 2230/30* (2013.01); *A61M 2230/50* (2013.01)

(58) Field of Classification Search
  CPC .......... A61M 16/0006; A61M 16/0051; A61M 16/0057; A61M 16/0063; A61M 16/0066; A61M 16/0069; A61M 16/021; A61M 16/022; A61M 16/024; A61M 16/026; A61M 16/04; A61M 16/0465; A61M 16/0488; A61M 16/049; A61M 16/06; A61M 16/0605; A61M 16/0627; A61M 16/0633; A61M 16/0666; A61M 16/0672; A61M 16/0677; A61M 16/0683; A61M 16/0694; A61M 16/0816; A61M 16/0833; A61M 16/085; A61M 16/0858; A61M 16/0875; A61M 16/10; A61M 16/101; A61M 16/1015; A61M 16/105; A61M 16/107; A61M 16/1075; A61M 16/109; A61M 16/12; A61M 16/122; A61M 16/125; A61M 16/16; A61M 16/161; A61M 16/201; A61M 16/202; A61M 16/203; A61M 16/204; A61M 2016/0021; A61M 2016/0024; A61M 2016/0027; A61M 2016/003; A61M 2016/0036; A61M 2016/0039; A61M 2016/0042; A61M 2016/101; A61M 2016/102; A61M 2016/1025; A61M 2016/103; A61M 2016/107; A61M 2016/125; A61M 2202/0208; A61M 2202/0275; A61M 2205/0238; A61M 2205/18; A61M 2205/3327; A61M 2205/3331; A61M 2205/3334; A61M 2205/3368; A61M 2205/50; A61M 2205/502; A61M 2205/505; A61M 2205/52; A61M 2205/6018; A61M 2230/005; A61M 2230/04; A61M 2230/06; A61M 2230/08; A61M 2230/10; A61M 2230/18; A61M 2230/202; A61M 2230/205; A61M 2230/30; A61M 2230/42; A61M 2230/432; A61M 2230/435; A61M 2230/50; A61M 2230/60; A61M 2230/62; A61M 2230/63; A61P 31/04; A61P 31/10; A61P 31/12; A62B 7/14; F04D 25/166; F04D 29/052; F04D 29/286; Y10T 137/2012

See application file for complete search history.

(56) References Cited

U.S. PATENT DOCUMENTS

| | | | | |
|---|---|---|---|---|
| 4,889,116 | A * | 12/1989 | Taube | A61M 16/00 128/204.23 |
| 4,963,327 | A * | 10/1990 | Russell | A62B 19/00 422/305 |
| 5,251,632 | A * | 10/1993 | Delpy | A61B 5/14553 600/323 |
| 5,682,877 | A | 11/1997 | Mondry | |
| 5,906,672 | A | 5/1999 | Michaels et al. | |
| 6,314,957 | B1 * | 11/2001 | Boissin | C01B 13/027 128/204.17 |
| 6,349,724 | B1 * | 2/2002 | Burton | F04D 29/052 128/204.22 |
| 6,786,217 | B2 * | 9/2004 | Stenzler | A61M 16/12 128/204.22 |
| 9,833,643 | B2 | 12/2017 | Squibb | |
| 9,907,926 | B2 * | 3/2018 | Allum | A61M 16/209 |
| 10,894,139 | B2 * | 1/2021 | Anderson | A61M 16/12 |
| 2005/0072423 | A1 * | 4/2005 | Deane | A61M 16/101 128/202.26 |
| 2005/0113709 | A1 | 5/2005 | Millet | |
| 2007/0077200 | A1 * | 4/2007 | Baker | A61M 16/12 424/9.1 |
| 2008/0066752 | A1 * | 3/2008 | Baker | A61M 16/107 128/204.23 |
| 2010/0292544 | A1 * | 11/2010 | Sherman | A61M 16/101 128/204.23 |
| 2011/0077474 | A1 | 3/2011 | Huiku | |
| 2014/0345609 | A1 * | 11/2014 | Whitcher | C01B 13/0259 128/202.26 |
| 2020/0368482 | A1 * | 11/2020 | Westfall | A61M 16/006 |

OTHER PUBLICATIONS

USPTO Final Office Action for U.S. Appl. No. 15/914,888 dated May 5, 2020.
USPTO Notice of Allowance for U.S. Appl. No. 15/914,888 dated Sep. 16, 2020.
USPTO Issue Notification for U.S. Appl. No. 15/914,888 dated Dec. 29, 2020.

* cited by examiner

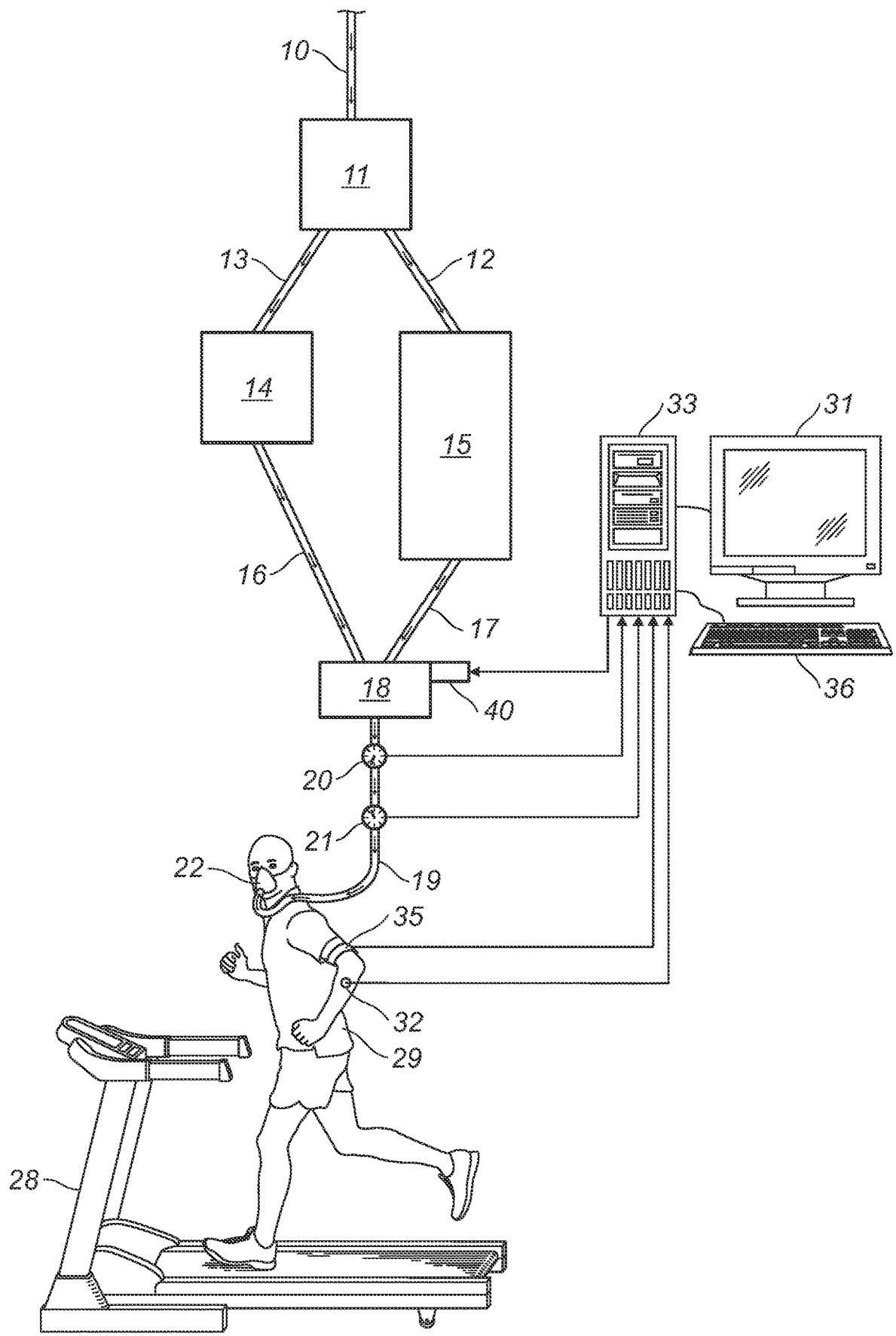

OXYGEN TREATMENT DEVICE FOR MAMMALS

This application is a continuation of U.S. patent application Ser. No. 15/914,888 filed Mar. 7, 2018, titled "Oxygen Treatment Device for Mammals", which claims priority to provisional application Ser. No. 62/619,387 filed Jan. 19, 2018, titled "Oxygen Treatment Device for Mammals", the entire content of which is incorporated herein by reference thereto.

BACKGROUND OF INVENTION

1. Field of the Invention

This invention is directed to a method and apparatus for regulating the concentration of oxygen in air delivered to a person for breathing. The apparatus and method can be used to improve the oxygen level in a person's blood and also to train an individual for athletic activities, (such as football, track and field) in geographical areas of higher elevation.

DESCRIPTION OF RELATED ART

Systems for delivering varying concentrations of oxygen to people for training purposes are known. However they are not designed to provide precise concentrations of oxygen. Also they do not include sufficient monitoring or measuring devices for the physiological measurements so that instantaneous information (such as heat rate, blood oxygen level, blood pressure as well as data related to the improvement of blood oxygen levels and other data compared to previous exercising sessions) can be calculated and displayed on a monitor.

This invention is adapted to supply a precise concentration of oxygen in air to a person for training or health reasons. The system includes a plurality of monitors and sensors for measuring the physiological characteristics of a person while exercising and at the same time displaying the information and comparing it to a previous test.

BRIEF DESCRIPTION OF THE DRAWING

The FIGURE is a schematic drawing showing the components of an apparatus according to one embodiment of the invention.

DETAILED DESCRIPTION OF THE INVENTION

As shown in the FIGURE, ambient air enters an oxygen concentrator 11 via conduit 10. Concentrated oxygen enters a closed reservoir 15 via conduit 12 and the exhaust leaves concentrator 11 via conduit 13 to a closed reservoir 14. The exhaust air his a lower concentration of oxygen than that of the ambient air.

Reservoirs 14 and 15 are connected to a valve 18 via conduits 16 and 17. Valve 18 is controlled via an actuator 40 by a central processing unit 33 to control the oxygen level of the air leaving valve 18. The air is a mixture of concentrated oxygen and the exhaust produced from concentrator 11. The air is conveyed to a breathing mask 22 via a conduit 19. Flow meter 20 and an oxygen concentration meter 21 may be located within conduit 19. The patient or athlete 2 is thus supplied air the oxygen content of which may be varied.

The patient or athlete 29 is subjected to physical activity for example a treadmill 28. The subject's blood pressure, heart rate, blood oxygen level and other physical characteristics are measured by sensors 35, 32 for example and the data is sent to the central processing unit 33. The central processing unit processes the data and can vary the oxygen concentration of the air supplied to the subject by wireless manipulation of the valve 18 by actuator 40 according to algorithms stored in the CPU.

A display device 31 is connected to the CPU so that real time information is visible to the subject. This information can include the subject's blood pressure, heart rate, oxygen blood level, temperature etc. A keyboard 36 for data input is also provided.

Information such as the subject's sex, height, weight, age, medical history etc. can be inputted to the CPU.

One use of the apparatus can be to train athletes for competition at higher altitudes. Valve 18 can be set to deliver an oxygen concentration level of about 21% which is normal. The subject will exercise to raise their heart beat rate to a target level. At that point the oxygen concentration of air is fed to the subject at the desired elevation which will be lower than 21% to simulate the less dense air at higher elevations. For example at 6000 ft the effective oxygen level is 16.6%. The effect of lowering the oxygen concentration on the subject's heartbeat, blood pressure and blood oxygen level can be monitored and stored in the CPU.

After a given period of time the oxygen concentration can be raised to 21% and the time it takes for the subject's heart rate to return to the baseline level can be measured as well as the oxygen blood level. Subsequent tests can be performed to measure the subject's improvement in recovery time and also in blood oxygen levels, as well as the subject's endurance. All this information can be displayed on display device 31 in real time and can be compared to prior tests.

Another use is to supply air with increased oxygen levels to a patient in order to raise the oxygen levels in a patient's blood. Repeated treatments have resulted in removing toxins from the blood and increasing blood oxygen levels. These results can have a positive effect on the functioning of a person's organs and an overall improvement in a person's health.

Reservoirs 14 and 15 may be fabricated using gas impermeable fabric or cloth and may be separate from each other or attached at a common point.

Display device 31 may include several screens so that different parameters may be displayed concurrently.

The sensors and flow meters may communicate with the CPU wirelessly and vice versa.

What is claimed is:

1. A method of delivering air to a person for treatment or training, comprising:

providing an oxygen treatment device comprising:

an oxygen concentrator, wherein the oxygen concentrator receives ambient air through a first conduit, and further wherein the oxygen concentrator comprises an outlet for oxygen and an outlet for exhaust air, a first closed reservoir, wherein the first closed reservoir is connected to the outlet for oxygen of the oxygen concentrator via a second conduit, a second closed reservoir, wherein the second closed reservoir is connected to the outlet for exhaust air of the oxygen concentrator via a third conduit, a mixing valve, wherein the mixing valve comprises an input for oxygen from the oxygen concentrator, an input for exhaust air from the oxygen concentrator, and an output for a mixture of exhaust air and oxygen from the oxygen concentrator, and further wherein the input for oxygen of the mixing valve is connected to the first closed reservoir via a fourth conduit, and further wherein the input for exhaust air of the mixing valve is connected to the second closed reservoir via a fifth conduit, an actuator, wherein the actuator controls the mixing valve, and further wherein the actuator is controlled by a central processing unit, a breathing mask, wherein the breathing mask is connected to the output for a mixture of exhaust air and oxygen of the mixing valve via a sixth conduit, wherein the sixth conduit is connected to a flow meter and an oxygen concentration meter, and further wherein the flow meter and the oxygen concentration meter are connected to the central processing unit, a plurality of physiological sensors connected to the central processing unit, wherein the plurality of physiological sensors comprises a blood pressure sensor, a heart rate sensor, and a blood oxygen sensor, and a display device, wherein the display device is connected to the central processing unit, and further wherein the central processing unit is programmed to control the mixing valve in response to inputs from the flow meter, the oxygen concentration meter, and the plurality of physiological sensors;

actuating the oxygen concentrator, wherein the oxygen concentrator sends concentrated oxygen into the first closed reservoir via the second conduit, and further wherein the oxygen concentrator also sends exhaust air into the second closed reservoir via the third conduit;

controlling the flow of the concentrated oxygen and the exhaust air by employing the mixing valve, wherein the concentrated oxygen and the exhaust air are mixed in specific proportions;

conveying the mixture of exhaust air and oxygen through the sixth conduit to the breathing mask;

measuring the blood pressure of a patient or athlete using the blood pressure sensor, wherein the blood pressure sensor sends blood pressure data to the central processing unit;

measuring the heart rate of the patient or athlete using the heart rate sensor, wherein the heart rate sensor sends heart rate data to the central processing unit;

measuring the blood oxygen level of the patient or athlete using the blood oxygen sensor, wherein the blood oxygen sensor sends blood oxygen level data to the central processing unit;

evaluating the blood pressure data, the heart rate data, and the blood oxygen level data;

varying the proportion of the concentrated oxygen to the exhaust air by wirelessly actuating the mixing valve in response to the evaluation of the blood pressure data, the heart rate data, and the blood oxygen level data; and displaying the current blood pressure data, heart rate data, and blood oxygen level data of the patient or athlete on the display device.

2. The method of claim 1, wherein the method further comprises inputting the sex, height, weight, and age of the patient or athlete into the central processing unit.

3. The method of claim 1, wherein the method further comprises:
setting the initial proportion of concentrated oxygen and exhaust air to have a 21% oxygen concentration;
setting a target heart rate for the patient or athlete; and
adjusting the oxygen concentration to below 21% when the target heart rate of the patient or athlete is reached.

4. The method of claim 1, wherein the initial oxygen concentration is set to 16.6%.

5. The method of claim 4, wherein the oxygen concentration is increased to 21% after a set amount of time.

6. The method of claim 1, wherein the first closed reservoir and the second closed reservoir are fabricated from impermeable fabric.

7. The method of claim 1, wherein the display of the current blood pressure data, heart rate data, and blood oxygen level data of the patient or athlete is displayed alongside the blood pressure data, heart rate data, and blood oxygen level data of the patient or athlete from a previous session.

\* \* \* \* \*